United States Patent [19]

Murphy

[11] 4,180,080

[45] Dec. 25, 1979

[54] ELECTRODE ASSEMBLY FOR SENSING HEART ACTIVITY

[75] Inventor: John B. Murphy, West Roxbury, Mass.

[73] Assignee: Hewlett-Packard Company, Palo Alto, Calif.

[21] Appl. No.: 899,049

[22] Filed: Apr. 24, 1978

Related U.S. Application Data

[63] Continuation-in-part of Ser. No. 838,501, Oct. 3, 1977, Pat. No. 4,149,528.

[51] Int. Cl.² .......................................... A61B 5/04
[52] U.S. Cl. .................................................. 128/642
[58] Field of Search .............. 128/2.06 E, 2.1 E, 404, 128/418, 419 P, DIG. 4, 642, 784, 785

[56] References Cited

U.S. PATENT DOCUMENTS

| | | | |
|---|---|---|---|
| 3,416,534 | 12/1968 | Quinn | 128/418 |
| 3,750,650 | 8/1973 | Ruttgers | 128/2.06 E |
| 3,827,428 | 8/1974 | Hon et al. | 128/2.06 E |
| 3,986,497 | 10/1976 | Dali | 128/2.06 E |
| 4,000,745 | 1/1977 | Goldberg | 128/418 |

FOREIGN PATENT DOCUMENTS

| | | | |
|---|---|---|---|
| 1316072 | 5/1973 | United Kingdom | 128/DIG. 4 |
| 1457426 | 12/1976 | United Kingdom | 128/2.06 E |
| 325018 | 2/1972 | U.S.S.R. | 128/419 P |

OTHER PUBLICATIONS

Hon et al., "Electronic . . . Fetal Heart Rate," Ob. & Gyn, vol. 40, No. 3, Sep. '72, pp. 362–365.

*Primary Examiner*—Lee S. Cohen
*Attorney, Agent, or Firm*—Stephen P. Fox

[57] ABSTRACT

An electrode assembly for sensing heart activity from body tissue includes a flexible guide tube, a spiral retaining coil disposed in one end of the guide tube, a handle disposed at the other end of the guide tube, and twisted wires inside the tube interconnecting the retaining coil and the handle. Rotation of the handle rotates the twisted wires, which in turn rotate the retaining coil to screw it into body tissue. A safety stop releasably disposed on the guide tube limits the rotation of the retaining coil and thus limits its depth of penetration into the body tissue. After the handle is rotated a preselected amount, the handle is automatically disengaged from the twisted wires.

10 Claims, 8 Drawing Figures

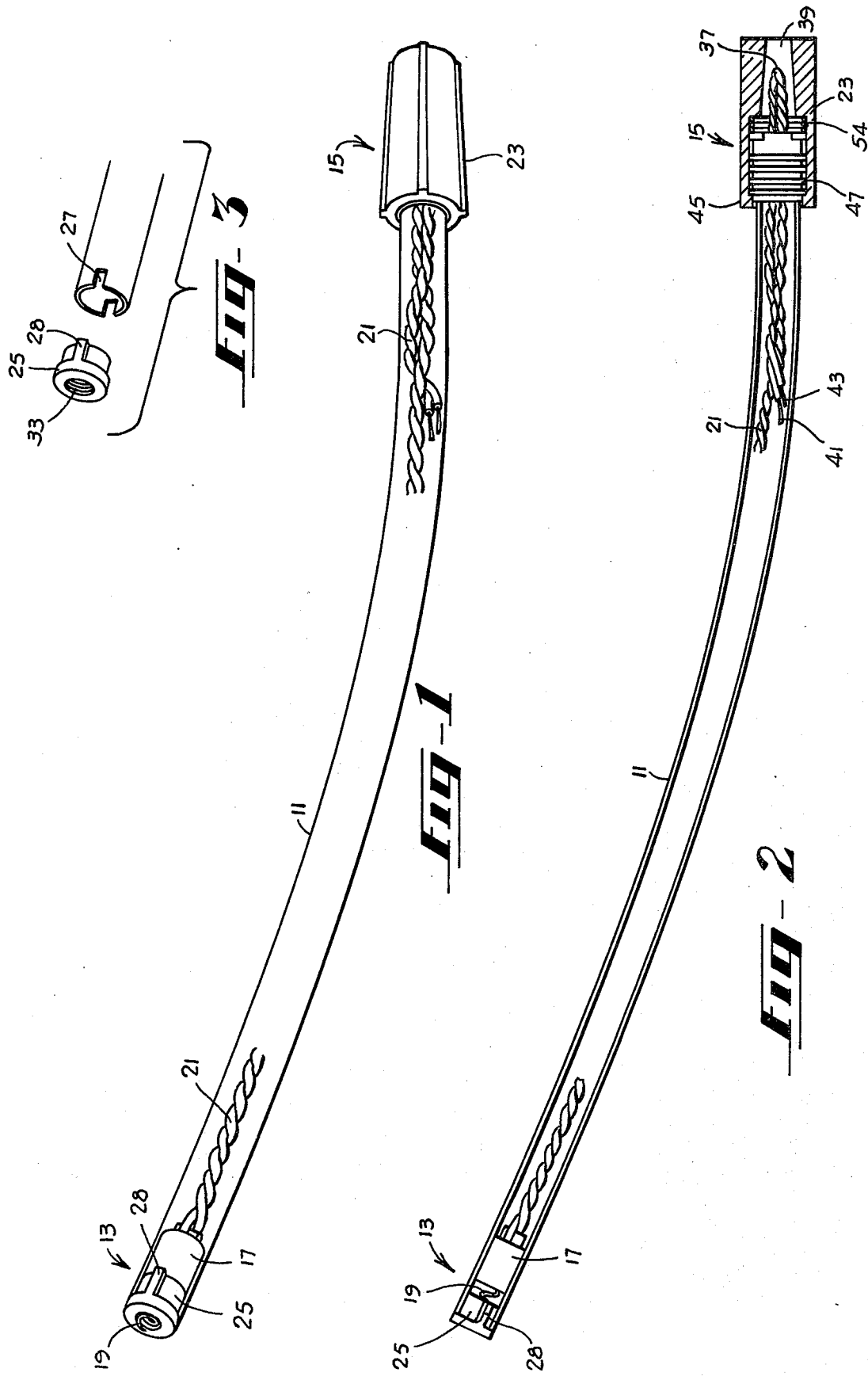

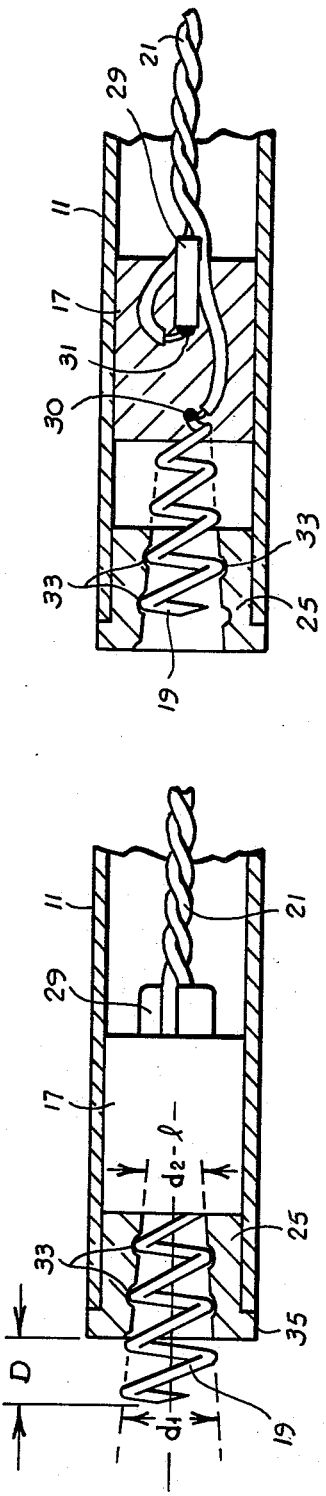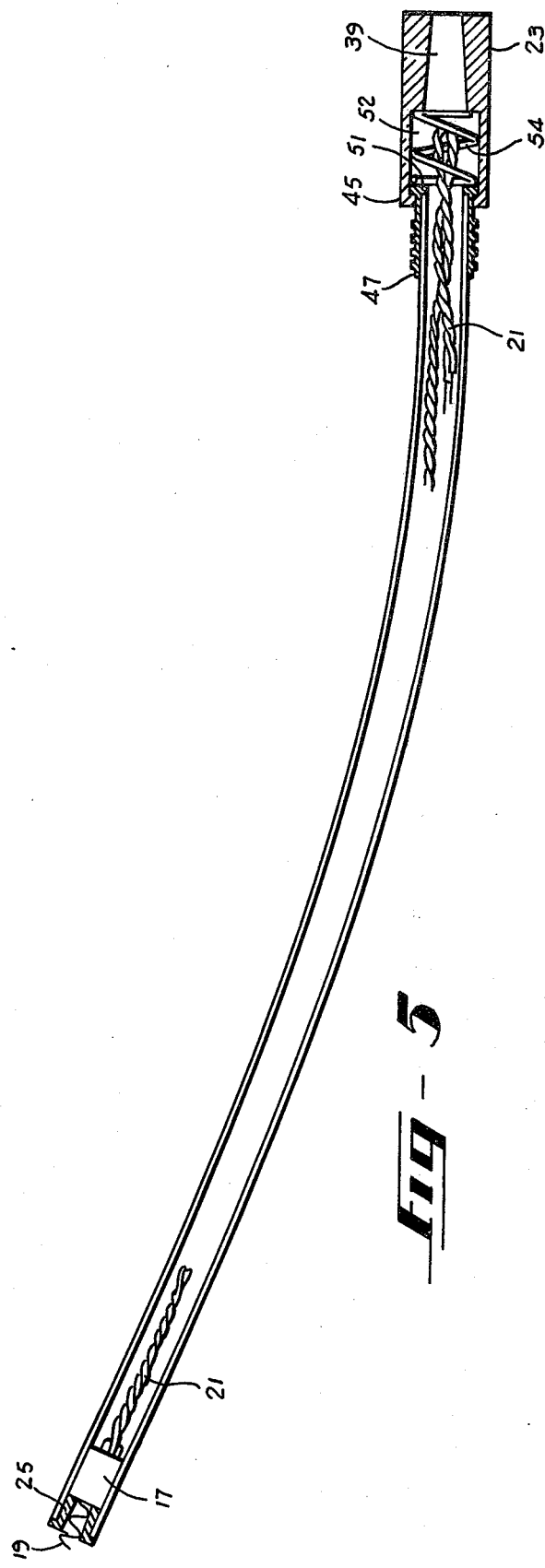

ELECTRODE ASSEMBLY FOR SENSING HEART ACTIVITY

CROSS-REFERENCE TO RELATED APPLICATION

The present application is a continuation-in-part of application Ser. No. 838,501 filed in the name of John B. Murphy on Oct. 3, 1977, now U.S. Pat. No. 4,149,528.

BACKGROUND OF THE INVENTION

This invention relates generally to an electrode assembly for attachment to body tissue to sense electrical heart activity. The electrode is particularly suited for insertion through the vaginal passageway of a woman in labor and for remote controlled attachment to the fetus. The electrode provides heart signals to electronic monitoring equipment which displays an electrocardiogram and/or the heart rate.

A variety of remote controlled insertion tools and electrodes have been proposed for use in the body. For example, MacLean U.S. Pat. No. 2,839,049 describes a guide tube for insertion in the vaginal canal. The guide tube contains a wire having a handle attached to one end and a brush attached to the other end. Rotation of the handle causes rotation of the brush inside the womb.

H. D. Junge discloses an electrode for attachment to a fetus in a paper entitled "Eine Neue Technik Der Elektronischen Daueruberwachung Von Fetaler Herzfrequenz Und Wehentåtigkeit Unter Der Geburt" published in *Geburtshilfe Und Frauenheilkunde,* Feb. 1969, pages 129–133. The electrode assembly includes a retaining coil mounted on a holder. The holder is coupled to a drive rod through releasable cooperating engaging means including prongs on the rod which engage depressions on the holder. The drive rod is disposed in a guide sleeve and the assembly is inserted into the vaginal canal until the retaining coil contacts the fetus. Thereafter, the external end of the rod is rotated, thereby to rotate the retaining coil and screw it into the fetus. The guide sleeve and drive rod are then removed from the vaginal canal and a signal lead extending from the retaining coil is attached to electronic heart monitoring apparatus.

Following the publication by H. D. Junge, others developed remote controlled electrode assemblies which screw retaining coils into body tissue. Ruttgers U.S. Pat. No. 3,750,650 discloses a fetal monitoring electrode assembly including a spiral electrode extending from a holder. A drive tube retains the holder by cooperating engaging means including slots in the drive tube and projections on the holder. In use the assembly is rotated to screw the spiral electrode into an unborn fetus. The guide tube and drive tube are then telescoped to release the electrode from the tubes and the two tubes are withdrawn from the vaginal canal.

Rasor U.S. Pat. No. 3,835,864 describes a remote controlled device for screwing a retaining coil into body tissue. The coil holder is rotated by a flexible drive rod inside a guide tube. The drive rod is coupled to the coil holder through cooperating engaging means which operates to release the coil holder from the drive rod after the coil is attached to the body tissue.

Hon, et al., U.S. Pat. No. Re. 28,990 also discloses a remote controlled device for screwing a retaining coil electrode into body tissue (a fetus) wherein the coil is rotated by a drive tube inside a guide tube. The drive tube is coupled to the coil by cooperating engaging means in the form of fins on the coil holder and slots in the drive tube.

One disadvantage inherent in electrode assemblies of the type described above is that they are characterized by complex insertion tool arrangements. Numerous components including guiding and driving tubes and releasable cooperating engaging means are required to achieve remote controlled rotation to screw the electrode coil into body tissue. These complex configurations are costly to manufacture and are often difficult to satisfactorily manipulate in use.

Another disadvantage of heretofore known electrode assemblies relates to the manner in which the electrode coil is applied to the body tissue. The retaining coil itself is usually small and formed with a few turns of sharply pointed stainless steel wire. When the coil is manually rotated by the insertion tool mechanism, it can easily be screwed deeply into body tissue. There is a danger that the electrode may be manually overdriven with consequent tearing of the tissue. In the case where the electrode coil is a few millimeters in diameter and applied through the vaginal canal to a fetus, the large torque transmitted by the insertion tool may drive the coil so deeply and tightly into the fetus that a plug of flesh is pulled out. Such coring by the electrode coil is traumatic to the fetus and precludes satisfactory electrode attachment for sensing heart activity.

SUMMARY OF THE INVENTION

The present invention provides a simplified electrode assembly which permits remote controlled rotation of an electrode coil without the aforementioned complex arrangement of guiding and driving tubes and releasable cooperating engaging means coupling the driving tube to an electrode holder. In addition, the present invention provides an electrode assembly in which the electrode coil penetration of the head of a fetus or other body tissue is limited to safe depths, on the order of a few millimeters, without danger of driving the coil too deeply or tightly into the body tissue.

The illustrated embodiment of the invention includes a flexible guide tube having a proximal end positionable adjacent to body tissue and a distal end remote from the body tissue. Disposed in the guide tube at the proximal end is a spiral retaining coil mounted on an electrode holder. Two twisted signal leads extend from the electrode holder through the guide tube to the distal end thereof. A rotatable handle on the distal end releasably engages the twisted signal leads. Rotation of the handle rotates the signal leads which in turn rotate the spiral retaining coil to screw it into body tissue.

A safety stop at the proximal end of the guide tube engages the spiral retaining coil and limits rotation of the coil, thereby to limit its depth of penetration into the body tissue. The handle is movable along the longitudinal axis of the guide tube and is spring biased to automatically disengage the handle from the twisted signal leads after preselected rotation of the handle. The automatic disengagement indicates proper attachment of the retaining coil to the body tissue and prevents over-rotation of the handle. Following attachment of the retaining coil to the body tissue, the guide tube is pulled off the signal leads which are then coupled to suitable electronic heart monitoring equipment.

BRIEF DESCRIPTION OF THE DRAWINGS

FIG. 1 is a perspective view of one embodiment of the electrode assembly of the present invention.

FIG. 2 is a longitudinal cross-sectional view of the electrode assembly.

FIG. 3 is an enlarged perspective view of a portion of one end of the electrode assembly.

FIG. 4(a) and 4(b) are enlarged cross-sectional views of one end of the electrode assembly.

FIG. 5 is another longitudinal cross-sectional view of the electrode assembly.

DESCRIPTION OF THE PREFERRED EMBODIMENT

Figure 6:
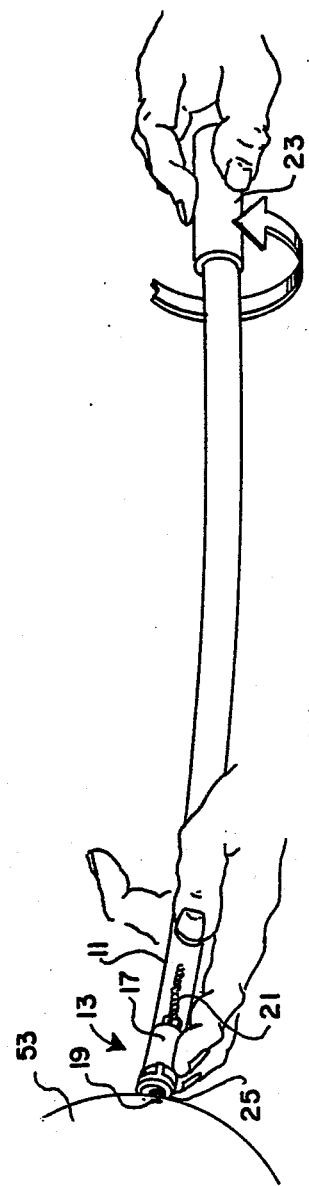
FIG. 6 is a perspective view illustrating use of the electrode assembly in attaching the electrode to body tissue.

Referring now to FIG. 1 there is shown an electrode assembly including a guide tube 11 having a proximal end 13 positionable against a fetus or other body tissue, and a remote distal end 15. The guide tube 11 is preferably constructed of a flexible plastic, such as polyethylene, and typically has an outside diameter on the order of eight millimeters. The flexible guide tube 11 is formed with a slight bend in it to facilitate insertion into body cavities, such as the vaginal passageway.

Disposed in guide tube 11 at the proximal end 13 is a rotatable electrode holder 17. Mounted on holder 17 is a spiral retaining coil 19 which is extendable from proximal end 13. A pair of twisted vinyl insulated wires 21 are attached to holder 17 and extend through guide tube 11 to the distal end 15. A handle 23 is mounted on the distal end 15 of the guide tube and coupled to the twisted wires 21. Rotation of handle 23 causes rotation of the wires 21, which in turn act as a drive member to rotate holder 17. The rotation of holder 17 rotates the spiral retaining coil 19 mounted thereon to extend from proximal end 13 and screw the coil into body tissue, as hereinafter described.

Disposed at the proximal end 13 of the guide tube is a safety stop 25 which is in the form of a ring having internal threads for receiving the spiral retaining coil 19. The spiral coil 19 is threaded into ring 25. Rotation of the holder 17 causes retaining coil 19 to be screwed through ring 25 and to extend beyond the ring. Ring 25 limits the extension of retaining coil 19 from the proximal end 13 of the guide tube by limiting the rotation of the coil, as described below.

FIG. 2 illustrates the electrode assembly in cross-section. At the proximal end 13, the safety stop ring 25 is releasably disposed in the end of guide tube 11. More particularly, as shown in FIG. 3, the end of the guide tube includes one or more slots 27 which engage protrusions 28 on the ring 25. Ring 25 may be disengaged from guide tube 11 by sliding it away from the guide tube along the longitudinal axis thereof.

FIGS. 4(a) and 4(b) are enlarged cross-sectional views of the proximal end 13 of the electrode assembly. With reference to the cross-section of holder 17 in FIG. 4(a), one of the two twisted wires 21 is connected to the end of spiral retaining coil 19 internally of holder 17 at point 30. The retaining coil 19 extends from a forward end surface of holder 17 toward the open end of the guide tube. On the rearward end surface of holder 17, there is mounted a plate-like electrode 29 which is connected to the other one of the twisted wires 21 at point 31. Thus, the two twisted wires 21 serve as electrical signal leads. The spiral retaining coil 19 functions as a first electrode, and the rearwardly extending plate 29 functions as a second electrode.

Holder 17 has a cylindrical configuration with an outside diameter which is slightly less than the inside diameter of guide tube 11, thereby to permit the holder to be rotated inside the guide tube by the torque applied to the signal lead wires 21. Ring 25 has internal threads 33 which have substantially the same pitch as the pitch of the spiral retaining coil 19. As holder 17 is rotated, retaining coil 19 is screwed into the threaded ring 25 until the forward end surface of holder 17 abuts the rearward end surface of ring 25, as shown in FIG. 4(b). The engagement of holder 17 with ring 25 terminates the rotation of the holder and thus limits the forward advancement of retaining coil 19 through the ring 25.

FIG. 4(b) illustrates holder 17 shifted 90 degrees from the position shown in FIG. 4(a), thereby to illustrate the side and top of plate 29 which forms the second electrode.

The spiral retaining coil 19 has a predetermined length along its longitudinal axis l, so as to permit the retaining coil to pass through ring 25 and extend beyond it a predetermined distance D. In the case where the retaining coil 19 is screwed into the head of a fetus, the dimension D is preferably on the order of two millimeters. By limiting the rotation of holder 17 and the forward advancement of retaining coil 19 out of the end of guide tube 11, the ring 25 acts as a safety stop. The penetration of spiral retaining coil 19 into the fetus or other body tissue is limited to safe depths. There is no danger that the coil will be driven too deeply and tightly into the body tissue. Nor is there any risk of tearing or coring the body tissue by over-driving the spiral retaining coil.

While holder 17 is screwed into ring 25, the ring is held against axial rotation by the protrusion 28 thereon which engages slot 27 in the guide tube 11 (see FIG. 2 and 3). As shown in FIG. 4(b), ring 25 includes a flange 35 which abuts against the proximal end of guide tube 11 to assist in holding the ring 25 in position at the end of the guide tube. The assembly of ring 25 and holder 17 may be slid out of the guide tube, as described hereinafter.

As shown in FIGS. 4(a) and 4(b), the retaining coil 19 is tapered such that it has an outside diameter which decreases from the pointed end along the longitudinal axis l of the coil toward the distal and of the guide tube. In particular, the diameter $d_1$ of coil 19 at the pointed end is on the order of one-half millimeter larger than the diameter $d_2$ at the other end of the coil. Similarily, the ring 25 into which coil 19 is screwed has a mating thread which is tapered to a smaller inside diameter along the longitudinal axis l toward the distal end of the guide tube. The arrangement of the tapered coil and ring provides a small frictional drag in screwing the coil into and through the ring and precludes the ring from coming off the coil in use.

With reference to FIGS. 2 and 5, rotation of the spiral retaining coil is achieved by rotating the handle 23 at the distal end of guide tube 11. FIG. 2 illustrates the electrode assembly before use, wherein the retaining coil 19 is only partially screwed into the ring 25. FIG. 5 illustrates the electrode assembly after the retaining coil 19 has been screwed into ring 25 until holder 17 abuts ring 25, thereby limiting further rotation.

As shown in FIG. 2, the twisted signal leads extend from the rear surface of holder 17 to the distal end 15 of the guide tube. At the distal end, the two twisted signal leads are folded back on themselves at point 37 and received by a slot 39 in the rearward portion of handle 23. The folded signal wires 21 return back up into guide tube 11 and terminate in two bare electrical conductor wires 41, 43.

Handle 23 shown in FIG. 5 is rotated 90 degrees from its position shown in FIG. 2. It can be seen that slot 39 has a tapered rectangular shape. The slot is dimensioned to firmly hold the looped portion of wires 21 in longitudinally slidable engagement therewith. Rotation of the handle 23 about its longitudinal axis will rotate the looped end of wires 21 and thus impart rotational motion to the wires 21 in guide tube 11.

Handle 23 includes an internally threaded cylindrical end portion 45 which threadedly engages an externally threaded collar 47 firmly affixed to the distal end of guide tube 11. The threads on handle 23 and collar 47 are of the "left-hand" type, so that rotation of the handle in a clockwise direction on collar 47 serves to unscrew the handle from the collar. As the handle 23 is unscrewed from collar 47, slot 39 moves away from the looped end of wires 21 until the wires are disengaged from the slot. Following such disengagement, continued rotation of handle 23 will not rotate wires 21. After handle 23 is unscrewed from the threads on collar 47, the handle is freely rotatable on the distal end of guide tube and held onto the distal end by a plurality of protrusions 51 forming a lip surrounding the circumference of the rearward end of collar 47.

More particularly, handle 23 is formed with an internal cavity 52. Disposed in cavity 52 is a coil spring 54 which is held in compression against the end of collar 47. Spring 54 biases handle 23 away from the distal end of the guide tube. After the handle is rotated a preselected amount to become unscrewed from collar 47, the spring 54 moves the internally threaded end portion 45 of handle 23 against the lip of collar 47 formed by protrusions 51. Thus slot 39 in the handle moves along the longitudinal axis of the guide tube to disengage the signal wires 21. It can be seen that in operation, the handle 23 is automatically disengaged from wires 21 after preselected rotation of the handle. The automatic disengagement occurs with an audible "click" as the spring causes the handle to snap against the lip of collar 47. The "click" indicates to the user that proper attachment of the retaining coil 19 to body tissue has been achieved. Over-rotation of the handle and signal wires 21 by the user is prevented.

The overall operation of the electrode assembly may be understood by reference to FIGS. 2 and 5. Initially, as shown in FIG. 2, the spiral retaining coil 19 is screwed partway into ring 25 and the tip of the coil is recessed from the end of the ring. Ring 25 and holder 17 are disposed in spaced apart relation, separated by a few turns of the retaining coil 19. At the distal end 15 of guide tube 11, handle 23 is threaded all of the way onto collar 47 and the folded wires 21 are inserted fully into slot 39. In use, handle 23 is manually rotated to impart torque to the wires 21, which in turn rotates holder 17 and screws the spiral retaining coil 19 into ring 25. After a few turns of handle 23, holder 17 stops against ring 25, as shown in FIG. 5. At this point, spiral retaining coil 19 extends a predetermined distance from the end of ring 25 and will not rotate further. Continued rotation of handle 23 will merely twist wires 21 more tightly while longitudinally displacing the handle on the threaded collar 47. Ultimately handle 23 is unscrewed from the collar 47 and spring 54 biases the handle against lip 51 to disengage the folded end of wires 21 from slot 39. Continued twisting of the wires ceases. Handle 23 becomes freewheeling at the distal end. It can be seen that the safety stop in the form of ring 25 at the proximal end 13 limits the extension of spiral retaining coil 19, while the automatic disengagement of the handle 23 from the looped wires 21 with continued rotation of the handle terminates the application of torque to holder 17 and prevents the assembly from being over driven by excessive manual forces.

Figure 7:
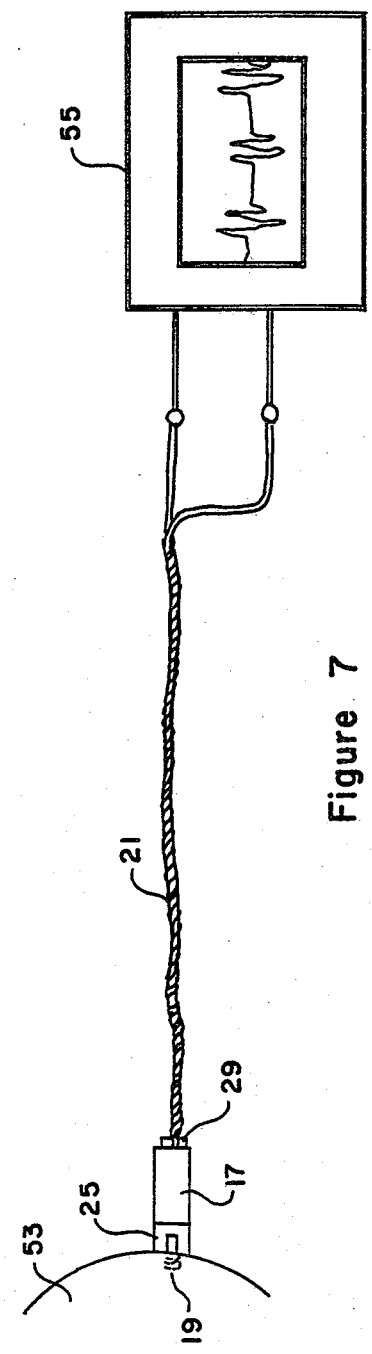
FIG. 7 is a diagramatic view illustrating use of the electrode with an electronic heart monitoring instrument.

FIG. 6 illustrates the electrode assembly as it is applied to body tissue before use in sensing heart activity. Body tissue 53 may be, for example, the head of a fetus or other fetal presenting part encountered by a doctor prior to delivery. Initially, the doctor applies the proximal end 13 of the assembly to the body tissue. Typically, the first two fingers of the left-hand are used to guide the proximal end 13 to make contact with the appropriate part of the body tissue 53. After contact is made, the doctor rotates handle 23 with his right-hand to screw spiral retaining coil 19 out of ring 25 and into the body tissue 53. After retaining coil 19 penetrates the body tissue to the permissible limit, as determined by the length of the coil 19 and the abutment of ring 25 with the coil holder 17 and after disengagement of the folded wires 21 at the distal end 15 from slot 39 in handle 23, the doctor pulls the guide tube 11 away from the body tissue 53, thereby to slide the guide tube off of ring 25, holder 17 and the attached wires 21. Thereafter, the exposed twisted wires 21 are unfolded at the distal end 15 and connected to a suitable monitoring instrument 55 as shown in FIG. 7. In the case where body tissue 53 is the head of a fetus, the spiral retaining coil 19 and the rearwardly extending plate 29 act as first and second bipolar electrodes, respectively, to sense fetal heart activity. The monitoring instrument 55 displays the fetal electrocardiogram and/or the fetal heart rate.

After application of the spiral retaining coil 19, the guide tube 11 and attached handle 23 may be discarded. Also, after use of the electrode for monitoring heart activity, the spiral retaining coil 19 is unscrewed from body tissue 53 by holding the ring 25 in one hand and rotating holder 17 counterclockwise with the other hand. Thereafter, the coil and holder assembly and attached wires may also be discarded.

I claim:

1. An electrode assembly for sensing heart activity from body tissue comprising:
   a guide tube having proximal and distal ends;
   an electrically conductive spiral retaining coil disposed in the proximal end of said guide tube and extendable from the proximal end;
   a signal lead attached to said retaining coil and extending through said guide tube to the distal end thereof;
   a handle disposed on the distal end of said guide tube in releasable engagement with said signal lead;
   said handle being rotatable to rotate said retaining coil by rotating said signal lead;
   said handle being movable along the longitudinal axis of said guide tube to permit disengagement of said handle from said signal lead; and a spring disposed at the distal end of said guide tube biasing said handle away from the distal end to disengage said handle from said signal lead after selected rotation of said handle.

2. The apparatus of claim 1, wherein said spring is disposed in said handle and in compression against the distal end of said guide tube to bias said handle away from said distal end along the longitudinal axis of said guide tube.

3. The apparatus of claim 2, wherein said spring is a coil spring.

4. The apparatus of claim 1, wherein said handle threadedly engages the distal end of said guide tube thereby to permit displacement of said handle from the distal end of said guide tube along the longitudinal axis of said guide tube by rotation of said handle.

5. The apparatus of claim 4, wherein said handle includes a slot releasably engaging said signal lead.

6. The apparatus of claim 5 wherein the slot in said handle is disposed on the longitudinal axis of said signal lead, thereby to permit longitudinal disengagement of the end of said signal lead from said slot by rotation of said handle.

7. The apparatus of claim 6, wherein said signal lead includes a pair of twisted wires folded back on themselves at the distal end of said guide tube and disposed in the slot in said handle.

8. The apparatus of claim 4, further including a collar having an externally threaded portion, said collar being attached to the distal end of said guide tube, and wherein said handle has an internally threaded portion releasably engaging said threaded collar.

9. The apparatus of claim 8, wherein said collar has a protruding lip portion displaced from said externally threaded portion along the longitudinal axis of said guide tube away from said distal end, and wherein said spring moves the internally threaded portion of said handle against the lip of said collar upon disengagement of the threaded portions of said collar and said handle.

10. An electrode assembly for sensing heart activity from body tissue comprising:
a guide tube having proximal and distal ends;
a rotatable electrode holder disposed in said guide tube at the proximal end thereof;
an electrically conductive spiral retaining coil mounted on said electrode holder and extending toward the proximal end of said guide tube;
a signal lead attached to said retaining coil and extending through said guide tube to the distal end thereof;
a rotatable drive member coupled to said holder and extending through said guide tube to the distal end thereof;
a handle disposed at the distal end of said guide tube and coupled to said drive member for rotating said drive member to rotate said holder and the spiral retaining coil mounted thereon; and
a safety stop disposed at the proximal end of said guide tube for limiting the rotation of said retaining coil, said safety stop including a ring releasably disposed on said proximal end and having an internal thread engaging said spiral retaining coil to permit said retaining coil to be screwed into said ring, said ring being engagable with said electrode holder upon predetermined rotation of said retaining coil to terminate rotation of said retaining coil;
said retaining coil having a decreasing outside diameter and said ring having a decreasing inside diameter along the longitudinal axes of said coil and said ring toward the distal end of said guide tube.

* * * * *